US008753292B2

(12) United States Patent
Ingold, Jr. et al.

(10) Patent No.: US 8,753,292 B2
(45) Date of Patent: Jun. 17, 2014

(54) METHOD FOR LOCATING A CATHETER TIP USING AUDIO DETECTION

(75) Inventors: James E. Ingold, Jr., Hillsborough, NC (US); Thomas Vincent Casey, II, Troy, NY (US); Brian F. Nentwick, Greenfield Center, NY (US)

(73) Assignee: AngioDynamics, Inc., Latham, NY (US)

( * ) Notice: Subject to any disclaimer, the term of this patent is extended or adjusted under 35 U.S.C. 154(b) by 257 days.

(21) Appl. No.: 13/251,686

(22) Filed: Oct. 3, 2011

(65) Prior Publication Data

US 2012/0083702 A1    Apr. 5, 2012

Related U.S. Application Data

(60) Provisional application No. 61/388,675, filed on Oct. 1, 2010.

(51) Int. Cl.
*A61B 5/00* (2006.01)

(52) U.S. Cl.
USPC .......................................................... 600/586

(58) Field of Classification Search
USPC .................................. 600/424, 585, 586, 593
See application file for complete search history.

(56) References Cited

U.S. PATENT DOCUMENTS

| | | | |
|---|---|---|---|
| 4,274,423 A | 6/1981 | Mizuno et al. |
| 4,821,731 A | 4/1989 | Martinelli et al. |
| 4,905,698 A | 3/1990 | Strohl, Jr. |
| 4,947,852 A | 8/1990 | Nassi et al. |
| 4,951,677 A | 8/1990 | Crowley et al. |
| 5,038,789 A | 8/1991 | Frazin |
| 5,042,486 A | 8/1991 | Pfeiler et al. |
| 5,078,714 A | 1/1992 | Katims |
| 5,099,845 A | 3/1992 | Besz et al. |
| 5,131,397 A | 7/1992 | Crowley |
| 5,156,157 A | 10/1992 | Valenta |
| 5,161,536 A | 11/1992 | Vilkomerson et al. |
| 5,280,786 A | 1/1994 | Wlodarczyk et al. |
| 5,386,828 A | 2/1995 | Owens et al. |
| 5,425,367 A | 6/1995 | Shapiro et al. |
| 5,526,820 A | 6/1996 | Khoury |
| 5,592,939 A | 1/1997 | Martinelli |
| 5,622,169 A | 4/1997 | Golden |
| 5,645,065 A | 7/1997 | Shapiro et al. |
| 5,666,958 A | 9/1997 | Rothenberg et al. |
| 5,727,552 A | 3/1998 | Ryan |
| 5,727,553 A | 3/1998 | Saad |
| 5,749,835 A | 5/1998 | Glantz |
| 5,843,076 A | 12/1998 | Webster |

(Continued)

OTHER PUBLICATIONS

Richard H. Brown, The Piezo Solution for Vital Signs Monitoring, Medical Design Technology, Mar. 11, 2008, pp. 36-40.

(Continued)

*Primary Examiner* — Max Hindenburg
(74) *Attorney, Agent, or Firm* — Ryan D. Artis (57) ABSTRACT

A method for locating a catheter tip within a human body is disclosed. An audio sensor is positioned at a site on the human body. An audio signal is detected by the audio sensor, and transmitted to an audio signal processing unit. The audio signal processing unit determines if the audio signal corresponds to a target location of the catheter tip, and transmits a notification signal to a user notification unit. An infusion of fluid or an audio emitting element can be used to generate the audio signal at the catheter tip.

3 Claims, 9 Drawing Sheets

(56) References Cited

U.S. PATENT DOCUMENTS

| | | | |
|---|---|---|---|
| 5,899,860 | A | 5/1999 | Pfeiffer et al. |
| 5,944,023 | A | 8/1999 | Johnson et al. |
| 5,983,126 | A | 11/1999 | Wittkampf |
| 6,038,468 | A | 3/2000 | Rex |
| 6,052,610 | A | 4/2000 | Koch |
| 6,061,588 | A | 5/2000 | Thornton et al. |
| 6,112,111 | A | 8/2000 | Glantz |
| 6,226,546 | B1 | 5/2001 | Evans |
| 6,230,042 | B1 | 5/2001 | Slettenmark |
| 6,261,247 | B1 | 7/2001 | Ishikawa et al. |
| 6,298,261 | B1 | 10/2001 | Rex |
| 6,304,769 | B1 | 10/2001 | Arenson et al. |
| 6,618,612 | B1 | 9/2003 | Acker et al. |
| 6,629,987 | B1 | 10/2003 | Gambale et al. |
| 6,690,963 | B2 | 2/2004 | Ben-Haim et al. |
| 6,705,319 | B1 | 3/2004 | Wodicka et al. |
| 6,711,429 | B1 | 3/2004 | Gilboa et al. |
| 6,741,883 | B2 | 5/2004 | Gildenberg |
| 6,977,504 | B2 | 12/2005 | Wright |
| 8,197,494 | B2 * | 6/2012 | Jaggi et al. ............ 606/130 |
| 8,512,256 | B2 * | 8/2013 | Rothenberg ............ 600/508 |
| 8,597,193 | B2 * | 12/2013 | Grunwald et al. ........ 600/468 |
| 2005/0157888 | A1 | 7/2005 | Yang |
| 2008/0097232 | A1 | 4/2008 | Rothenberg |

OTHER PUBLICATIONS

Tip Location of Peripherally Inserted Central Catheters, Journal of Vascular Access Devices, Summer 1998.

PICC Tip Location: Hot Topics: UI Community HomeCare: University of Iowa Health Care; www.uihealthcare.com/depts/uihomecare/hottopics/picctiplocation.html; Jul. 17, 2009.

Discover Sherlock* | Sherlock* II Tip Location System | Bard Access Systems; www.bardaccess.com/discoversherlock//sherlock_system.php, Jul. 17, 2009.

Piezo Film Sensors Technical Manual; Measurement Specialties; P/N 1005663-1 Rev B; Apr. 2, 1999.

* cited by examiner

METHOD FOR LOCATING A CATHETER TIP USING AUDIO DETECTION

CROSS-REFERENCE TO RELATED APPLICATIONS

This application claims priority to U.S. provisional application No. 61/388,675 filed on Oct. 1, 2010 incorporated herein by reference in its entirety.

TECHNICAL FIELD

The present invention relates generally to a method for locating a catheter tip within a human body. More specifically, the invention relates to a method for locating a catheter tip by detecting audio signals emitted from the catheter tip, processing the detected audio signals, and verifying that the catheter tip is at the target location.

BACKGROUND OF THE INVENTION

Medical professionals commonly use catheters for gaining prolonged access to an area within the body. Once the catheter tip is positioned at the target location, treatments such as antibiotics; chemotherapy, pain medicine, and nutrition can be administered. However, if the catheter tip is improperly positioned during insertion, or if the catheter tip migrates out of position after insertion, various risks arise, including a fluid infusion that causes pain or injury to the patient, complications due to increased thrombosis rates, delays in therapy, catheter malfunction and additional costs.

The general standard for proper catheter insertion depends on the type of catheter and the type of treatment. For example, peripherally inserted central catheters (or PICC lines) are commonly inserted into a brachial, cephalic or basilic vein in the arm and advanced through the venous system towards the superior vena cava. Current medical standards recommended that the distal tip of the catheter terminate in the lower ⅓ of the superior vena cava, close to the junction of the superior vena cava and the right atrium. However, since PICCs are commonly inserted into a vein in the arm and advanced through the venous system to reach the superior vena cava, the PICC line tip may be inadvertently positioned in a non-target area, such as the internal jugular or subclavian vein. Further, even if a PICC is property inserted, the catheter tip could later shift out of position if for example the patient coughs violently, moves a lot, or experiences severe vomiting. Therefore, verifying that the catheter tip is in the correct location is essential for safe operation of the catheter.

Catheter tip location techniques have improved the ability of medical professionals to verify the location of the catheter tip. One technique uses fluoroscopy to confirm tip location. Fluoroscopy provides the operator with real-time images of the patient's anatomy using a fluoroscope. Another technique uses electromagnetic detection and a stylet having an electromagnetic sensor placed inside the lumen of the catheter tip. Electromagnetic systems use an external device positioned directly over the internal target area for generating a magnetic field outside of the body. The electromagnetic sensor on the stylet is then inserted into the body through the catheter lumen and measures when the magnetic flux is at its greatest. A monitor indicates to the user when the electromagnetic sensor on the stylet is centered underneath the external device. In a variation of this technique, the external device senses the electromagnetic field, and an element at the tip of the stylet generates the electromagnetic field. Another technique uses ultrasound for guidance and determining catheter tip location. Electrocardiogram technology is also used determine catheter tip location by measuring the change of the P wave as the catheter progresses down the superior vena cava.

However, the systems and techniques described above have numerous deficiencies. Fluoroscopy requires a facility with fluoroscopy machine, and poses x-ray risks for both the patient and the operator. Further, interpreting the image in fluoroscopy and ultrasound can be difficult, and requires special training. Electromagnetic detection requires a stylet having an electromagnetic detecting or emitting component, and measurement accuracy can be disrupted by electromagnetic interference. Further, for patients with pacemakers or skin disorders, or for patients that are obese, device operability may dramatically decrease or be contraindicated. Electrocardiogram detection requires a normal sinus rhythm, and cannot indicate when the catheter tip is in locations including the jugular vein and the subclavian. Additionally, the technology associated with the tip location systems mentioned above can be cost prohibitive, decreasing the number of facilities properly equipped to perform catheter insertion and maintenance procedures.

Therefore, a new method of locating a catheter tip within a human body is desired in order to overcome or minimize the deficiencies described above.

SUMMARY

The present invention is directed to a method of locating a catheter tip within a human body using audio detection.

In one embodiment, a method for locating a catheter tip within a human body includes positioning an audio sensor at a site on the human body and infusing fluid through an opening in the catheter tip. An audio signal is detected through and transmitted to an audio signal processing unit. The audio signal processing unit determines if the audio signal corresponds to a target location of the catheter tip, and transmits a notification signal to a user notification unit.

In another embodiment, a method for locating a catheter tip within a human body includes inserting a catheter into a hollow anatomical structure of the human body. The catheter includes an elongated body having a proximal end and a distal end terminating in a catheter tip, a lumen having an opening disposed at the distal end, and an audio emitting element configured at a distal portion of the elongated body. The catheter is advanced at least partially through the hollow anatomical structure. An audio sensor is positioned at a site on the human body. An audio beacon signal is emitted from the audio emitting element, and an audio signal is detected through the audio sensor and transmitted to the audio signal processing unit. The audio signal processing unit determines if the audio signal corresponds to a target location of the catheter tip, and transmits a notification signal to a user notification unit.

In another embodiment, a method for locating a catheter tip within a human body includes inserting a catheter into a hollow anatomical structure of the human body. The catheter includes an elongated body having a proximal end and a distal end terminating in a catheter tip, and a lumen having an opening disposed at the distal end. An audio emitting element is positioned at the catheter tip. The catheter is advanced at least partially through the hollow anatomical structure. An audio sensor is positioned at a site on the human body. An audio beacon signal is emitted from the audio emitting element and an audio signal is detected through the audio sensor and transmitted to an audio signal processing unit. The audio signal processing unit determines if the first audio signal corresponds to a target location of the catheter tip, and transmits a notification signal to a user notification unit.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIGS. 4A-4D show various catheter tip positions and a corresponding user console display according to an example embodiment.

FIGS. 5A-5C show a piezo film audio sensor.

FIGS. 8A-8D show example embodiments of an audio emitting element located at the catheter tip.

DETAILED DESCRIPTION OF THE INVENTION

The present invention can be understood more readily by reference to the following detailed description, the examples included therein, and to the Figures and their following description. The drawings, which are not necessarily to scale, depict selected preferred embodiments and are not intended to limit the scope of the invention. The detailed description illustrates by way of example, not by way of limitation, the principles of the invention. The skilled artisan will readily appreciate that the devices and methods described herein are merely examples and that variations can be made without departing from the spirit and scope of the invention. It is also to be understood that the terminology used herein is for the purpose of describing particular embodiments only and is not intended to be limiting.

Referring now in detail to the drawings, in which like reference numerals indicate like parts or elements throughout the several views, in various embodiments, presented herein is a method for locating a catheter tip by audio detection.

Figure 1:
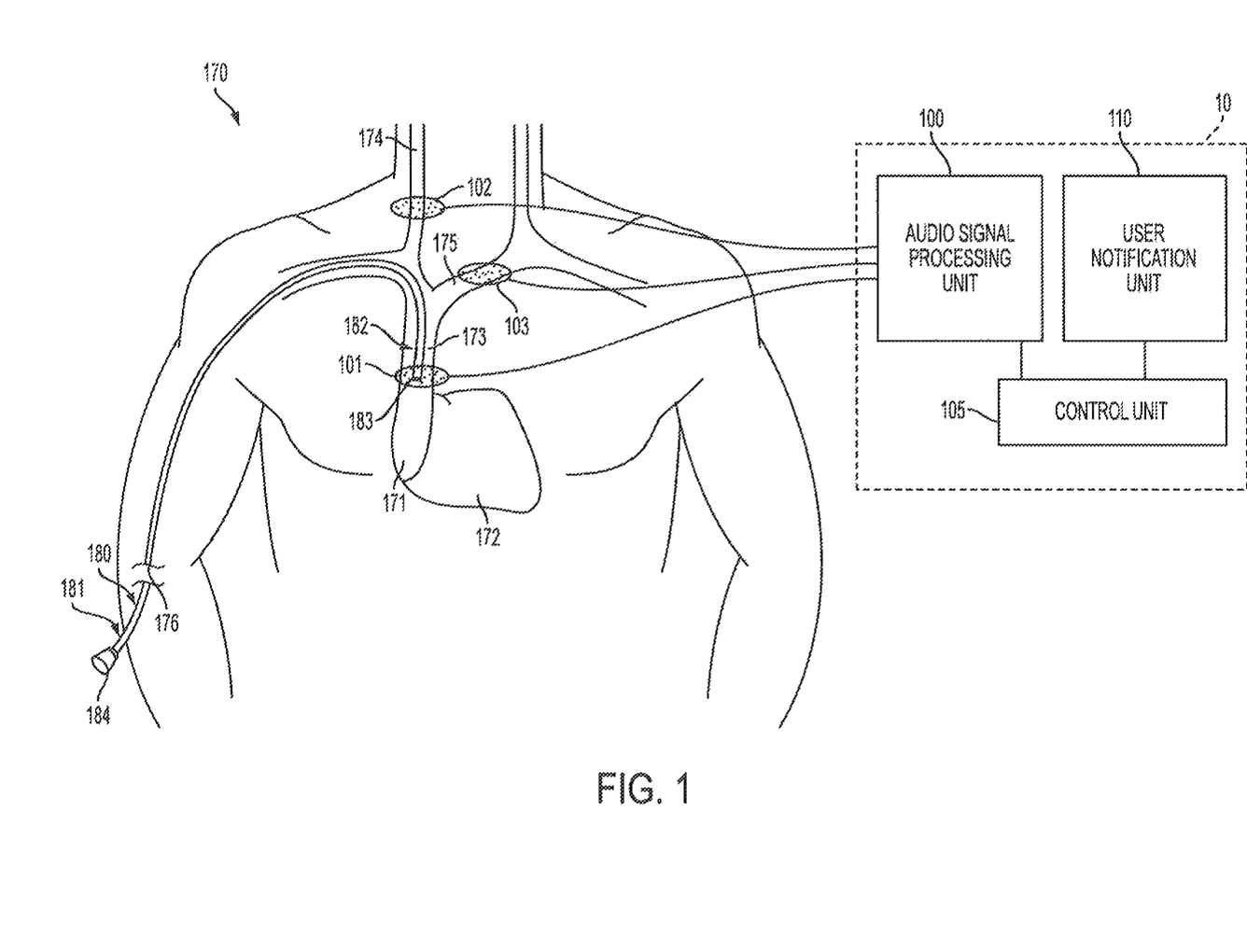
FIG. 1 is a view illustrating an application of the method according to an example embodiment of the present invention.

FIG. 1 shows a human body 170 with a catheter 180 inserted at a site 176 in the right arm. The catheter 180 has a proximal portion 181 and a distal portion 182. In the present embodiment, the catheter 180 is a single lumen catheter, but it can have multiple lumens. The proximal portion 181 of the catheter 180 terminates at the luer 184. The distal portion 182 of the catheter 180 terminates in a catheter tip 183. As shown in FIG. 1, the catheter 180 can be advanced to a target location, such as the superior vena cava 173, or some other site within the human body 170, for delivery of fluids such as antibiotics, chemotherapy, pain medicine, nutrition, or for withdrawing blood. The user console 10 is a device, such as a handheld tablet device, which houses the audio signal processing unit 100 and a user notification unit 110 for communicating with a user. Audio signals emitted from the catheter tip 183 are detected by one or more audio sensors 101, 102 or 103, transmitted to the audio signal processing unit 100, and processed for determining the location of a catheter tip 183. Once the catheter tip location is determined, the audio signal processing unit 100 sends a user notification signal to the control unit 105, which communicates with the user notification unit 110 to notify the user. The user notification unit 110 can utilize a visual display, a sound notification, or some combination of the two for communicating with the user.

Figure 2:
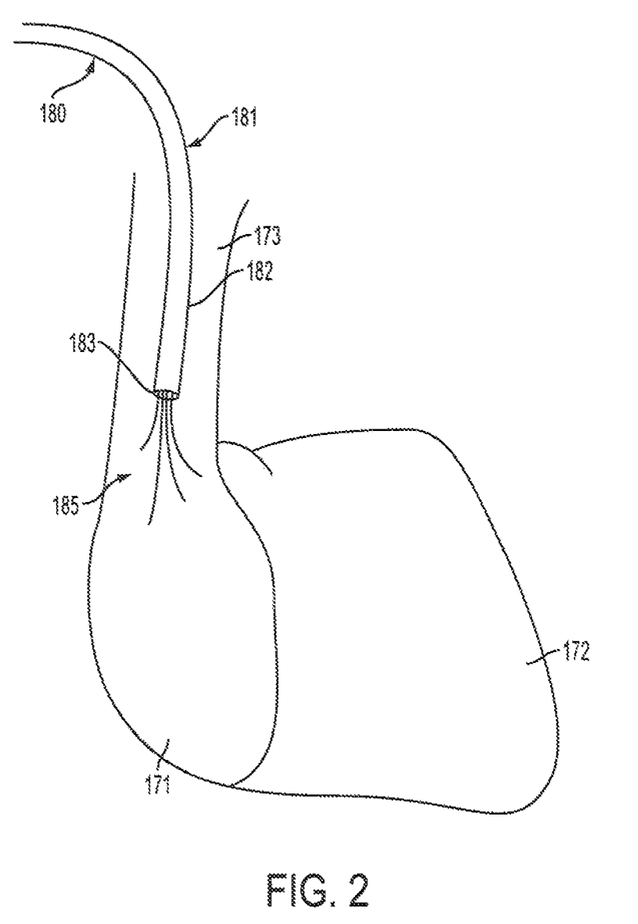
FIG. 2 is a cutaway view of a heart being accessed by a catheter infusing a fluid bolus.

As illustrated in FIG. 2, fluid can be rapidly injected into the lumen of catheter 180 and infused through an opening in the catheter tip 183. As the fluid 185 ejects through the opening, an audio frequency sound wave is generated. A fluid injection technique called push pause or push stop can be used to infuse fluid through the catheter 180. The push pause technique creates fluid turbulence at the catheter tip 183, generating an audio frequency sound wave. Increased fluid turbulence facilitates an increase in the intensity of the generated audio frequency sound wave. For example, a 10 mL syringe can be filled with 10 mL of saline and connected to the luer 184. Cycles of 2 mL of saline infused over 0.5 seconds followed by a 0.5 second pause can be repeated until the 10 mL of saline is fully infused. Other techniques for fluid infusion may be used according to the present invention so that an audio frequency signal capable of detection is generated at the catheter tip. Additionally, the viscosity of the fluid and the pressure applied to the syringe by the user can be manipulated to increase the flow rate of the fluid. An increased flow rate may also increase the intensity of the generated audio frequency sound wave, facilitating stronger detection signals.

Referring back to FIG. 1, the target location for the catheter tip 183 is just outside of the heart 172 in the lower ⅓ of the superior vena cava 173. A first audio sensor 101 is placed on the anterior side of the body 170, positioned directly above the lower ⅓ of the superior vena cava 173. When a saline bolus is flushed through the opening in the catheter tip 183, the first audio sensor 101 will detect and measure the emitted audio frequency signal. Utilizing only the first audio sensor 101, the audio signal processing unit 100 can indicate whether or not the catheter tip 183 is the lower ⅓ of the superior vena cava. The determination can be made by implementing audio signal processing techniques known in the art described in further detail below, including filtering the detected audio signal to detect the saline bolus, and comparing the intensity of the detected audio signal to a baseline signal or a predetermined threshold level.

In an alternative embodiment, a second audio sensor 102 is placed on the skin above the internal jugular vein 174. If, for example, the catheter tip 183 is unintentionally advanced to the internal jugular vein 174, the second audio sensor 102 will detect the audio signal emitted from the saline bolus. Additionally, an absent or weak audio signal will be detected by the first audio sensor 101, since the audio signal will attenuate over distance. The absent or attenuated audio signal detected by the first audio sensor 101 is an indication that the catheter tip is in the wrong position. Additionally, if the catheter is fully inserted, the absence of a detected audio signal from both audio sensors could indicate that the catheter tip has advanced to the subclavian vein, a malfunction occurred in one of the sensors, or that the catheter is malfunctioning, blocking the saline bolus from infusing through the opening in the catheter tip.

In an alternative embodiment, a third audio sensor 103 is placed on the skin above the subclavian vein 175. Thus, if the catheter tip 183 is unintentionally advanced to the subclavian vein 175, or becomes mispositioned after insertion, the third audio sensor 103 will detect the audio signal from the saline bolus. Additionally, with respect to the first and second audio sensors, no audio signal, or a weak audio signal attenuated by distance may be detected. Further, when the catheter tip is positioned in a non-target location (e.g. the internal jugular vein or the subclavian vein), the addition of the third sensor provides the audio signal processing unit 100 with enough data for identifying specifically which non-target position the catheter tip is located in.

In an alternative embodiment, first and second audio sensors 101 and 102 can be strategically placed for comparing detected audio signals and localizing the position of the catheter tip 183. For example, the right third intercostal space is commonly used by medical professionals as an external reference point for locating the superior vena cava 173. Accordingly, a first audio sensor 101 can be positioned on the skin directly above the second intercostal space and a second audio sensor 102 can be positioned on the skin directly above the fourth intercostal space. The first and second audio sensors 101 and 102 should be in alignment with each other and consequently roughly equidistant from the third intercostal space. As the catheter tip 183 is advanced down the superior vena cava 173, the intensity of the audio signal detected from the first audio sensor 101 will reach a maximum once the catheter tip 183 is directly under the second intercostal space. As the catheter 180 advances from the second intercostal space towards the third intercostal space, the intensity of the audio signal detected by the first audio sensor 101 will decrease as the intensity of the audio signal detected by the second audio sensor 102 increases. Eventually, the intensity of the signals detected by the first and second audio sensors 101 and 102 will equalize as the catheter tip 183 is centered directly below the third intercostal space. According to this alternative embodiment, the audio signal processing unit 100 can compare the first and second detected audio signals for localizing the catheter tip 183.

In an alternative embodiment, a fourth audio sensor can be placed on the skin above a right portion of the subclavian vein. In some instances, the catheter tip 183 returns down the same path from which it was inserted, for example, in a right portion of the subclavian. This could happen if for example the patient moves a lot during insertion and the catheter tip changes 180 degrees in direction, or the catheter tip become mispositioned after initial insertion. Thus, by placing a fourth audio sensor over a right portion of the subclavian, the audio signal processing unit 100 can detect the catheter tip 183 and alert the user.

Figure 3:
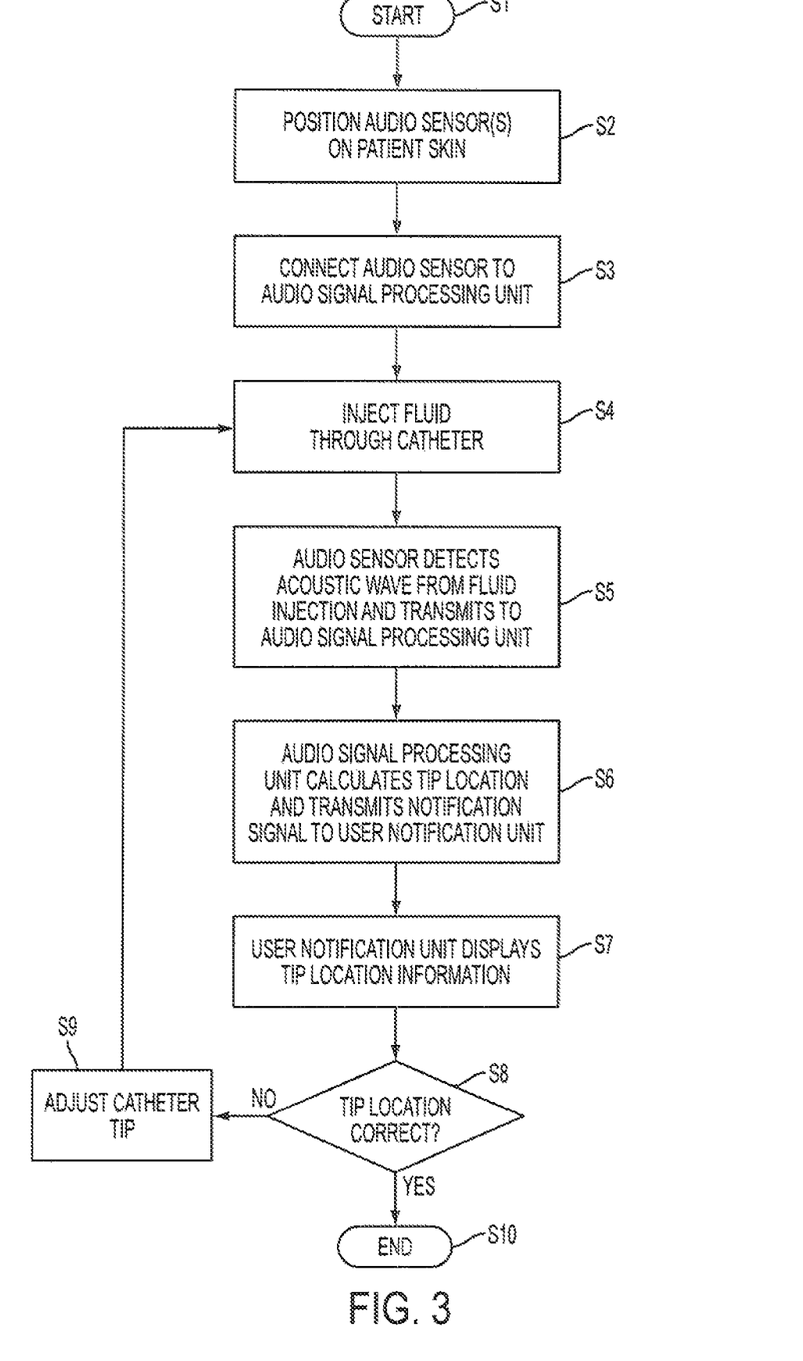
FIG. 3 is a flow chart of the method according to an example embodiment of the present invention.

Referring now to FIG. 3, a flow chart shows an example embodiment of the method according to the present invention. The patient may be undergoing a procedure for catheter insertion, or maintenance of a previously inserted catheter S1. At least one audio sensor 101 is placed above the patient's skin over the target area of the catheter tip 183 S2. The audio sensor 101 is connected or synced to the audio signal processing unit 100 S3. Fluid is injected through the catheter 180 S4 so that an audio frequency sound wave is generated at the catheter tip 183. The audio sensor 101 will detect the audio frequency sound wave generated from the fluid infusion, and the detected audio signal will be transmitted to the audio signal processing unit 100 S5. The audio signal processing unit 100 processes the detected audio signal and transmits a determination regarding tip location to the user notification unit 110 S6. The user notification unit 110 displays the tip location determination to the user S7. If the tip location is in the target location S8, the process has ended S10, as the catheter tip 183 is determined to be in the target location. If the catheter tip 183 is in a non-target location, or if the tip location cannot be determined S8, the user adjusts the catheter tip 183 S9 and injects more fluid through the catheter 180 S4. A new audio frequency sound wave generated from the fluid infusion is detected and transmitted to the audio signal processing unit 100 S5. The audio signal processing unit 100 processes the new signal, sends the determination of tip location to the user notification unit 110 S6, and communicates that determination to the user S7. If the tip is in the target location S8, the process ends S10. Otherwise, the user may repeat steps S4 through S9 multiple times until the catheter tip 183 is in the target location. Thus several advantages of one or more aspects according to this example embodiment are that the catheter tip of any catheter can be located, regardless of length, size or manufacturer. Further, there is no need for a separate stylet component, electromagnetic detecting or emitting components, or a patient with a normal sinus rhythm. In addition, the patient is not exposed to harmful radiation, and the operator does not need special training in interpreting x-ray or ultrasound images.

Figure 4A:
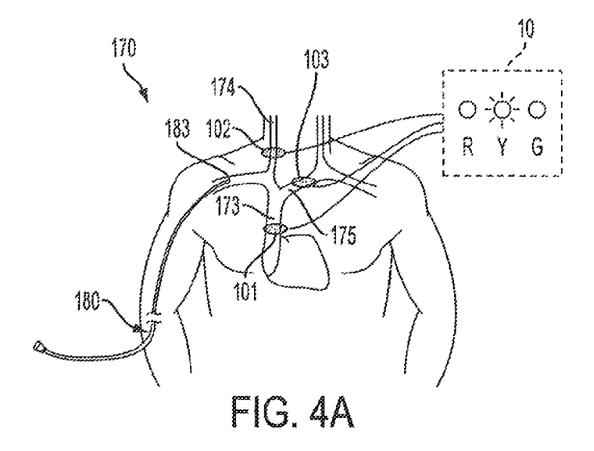
FIG. 4A shows a user console display when a catheter tip is positioned in a vein in the shoulder.
Figure 4B:
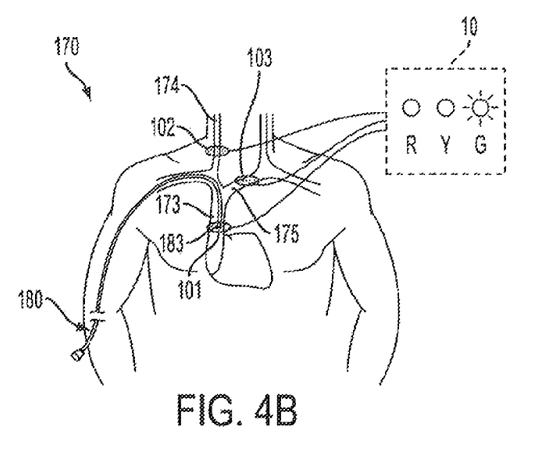
FIG. 4B shows a user console display when a catheter tip is positioned in the lower ⅓ of the superior vena cava.
Figure 4C:
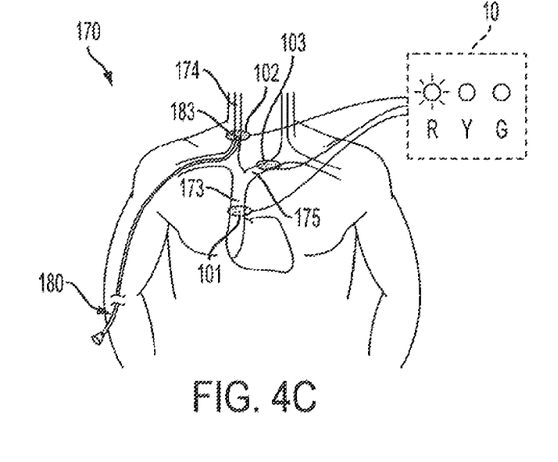
FIG. 4C shows a user console display when a catheter tip is positioned in the internal jugular vein.
Figure 4D:
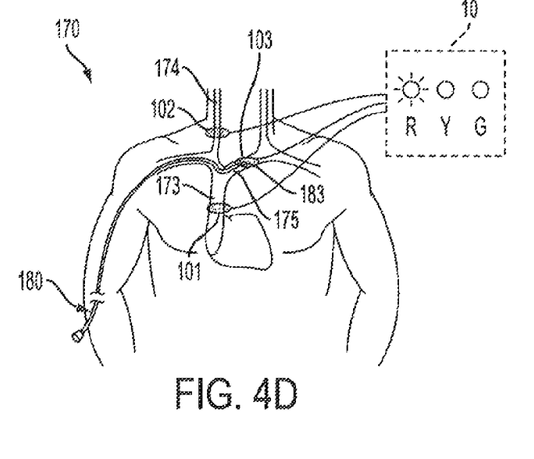
FIG. 4D shows a user console display when a catheter tip is positioned in the subclavian vein.

After the audio signal processing unit 100 determines whether or not the detected audio signal corresponds to the target catheter tip location, a notification signal is sent to a user notification unit 110. The notification signal can be sent either directly to the user notification unit 110, or sent to a control unit 105 that communicates with the user notification unit 110. The user notification unit 110 can have a visual display for indicating when the catheter tip 183 is in proper position. FIGS. 4A-4D illustrate a user notification display on the user console 10 according to an example embodiment. Depending on the determination made by the audio signal processing unit 100, the user notification unit 110 will display a red light indicating that the catheter tip 183 has been located and is not in the target location, a yellow light indicating that the catheter tip 183 has not been located, or a green light indicating that the catheter tip 183 has been located and is in the target location. Thus, as shown in FIG. 4A, if the catheter tip 183 is located too far away from any one of the sensors, an audio signal emitted from the saline bolus will not be detected, and the yellow light will activate. FIG. 4B shows the catheter tip 183 in the target location of the lower ⅓ of the superior vena cava. The audio signal processing unit 100 will verify that catheter tip in the proper location, thus activating the green light. FIGS. 4C and 4D show the catheter tip 183 after being mispositioned or migrating to the internal jugular vein 174 and the subclavian vein 175 respectively, activating the red light. The user notification signal can also take other forms, including an audio notification or a message display.

Figure 5A:
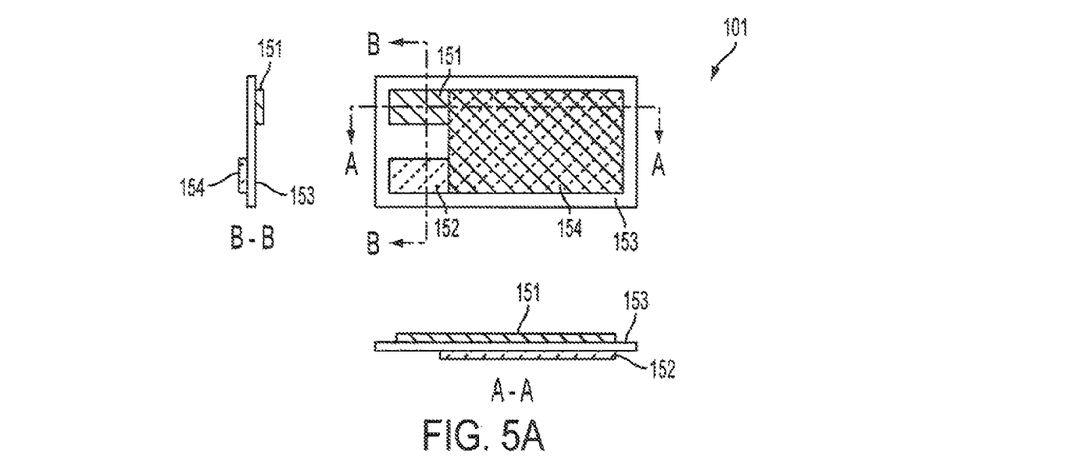
FIG. 5A is a top view of a piezo film audio sensor, including cross-sectional views A-A and B-B.
Figure 5B:
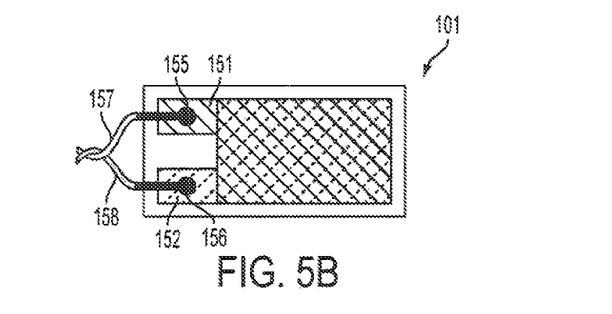
FIG. 5B is a top view of a piezo film audio sensor with lead attachments.
Figure 5C:
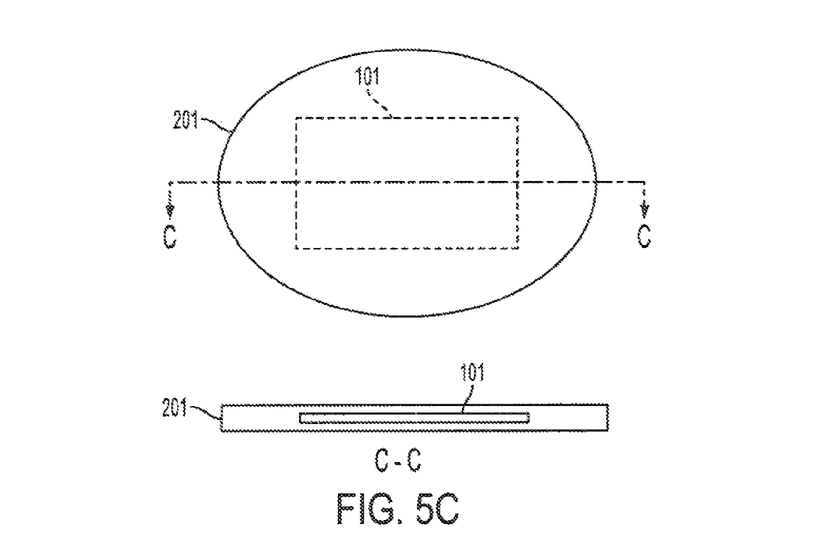
FIG. 5C is a top view of an audio sensor within a protective layer, including cross-sectional views C-C.

FIGS. 5A-5C show an example embodiment of an audio sensor 101. The audio sensor 101 can be any audio sensor or microphone element capable of detecting audio signals emitted from within the human body. In the present embodiment, the audio sensor is made of piezoelectric polyvinylidene fluoride polymer film (PVDF or piezo film). Piezo film is used for various acoustic applications, including contact microphones for detecting sounds emitted from within a, human body. Piezo film is a flexible, lightweight, highly sensitive thin film capable of being used as an audio sensor. Piezo film is also immune to moisture, and requires no external power to function, unlike electrostatic types of audio sensors. FIG. 5A shows an example embodiment of a piezo film audio sensor, with an upper electrode 151, a lower electrode 152, and a piece of piezo film 153 configured between the upper and lower electrodes. The electrodes are silver ink screen printed electrodes, which offer high conductivity, high flexibility and a thin profile. The upper electrode 151 and lower electrode 152 overlap at the active piezo film area 154. When the piezo film 153 is stretched, an electrical signal is generated between the upper electrode 151 and lower electrode 152 surfaces at the active piezo film area 154. The electrical signal is proportional to the amount of elongation of the piezo film 153. The piezo film sensor may be combined with a low-noise electronic preamplifier, and designed to minimize external acoustic noise.

Transmission of detected audio signals to the audio signal processing unit 100 can be accomplished by either hard wired or wireless transmission. As shown in FIG. 5B, lead attachments 155 and 156 can be configured on the upper electrode 151 and lower electrode 152 using a number of methods, including for example, eyelets, compression clamping, rivets, crimping, eyelet holes or low temperature solders. The example embodiment in FIG. 5B shows a first rivet 155 connecting a first wire 157 to the upper electrode 151 and a second rivet 156 connecting a second wire 158 to the lower electrode 152. Lightweight shielded cable or twisted wire pairs can be used to connect the audio sensor 101 to the audio signal processing unit 100 while also reducing vulnerability from unwanted electromagnetic interference.

Now with reference to FIG. 5C, the audio sensor 101 can be designed to vibrate the piezo film through a medium, such as a pad, protective coating or protective layer 201. The protective layer 201 may be in direct physical contact with the skin when placed on the body. The protective layer 201 can be made of a material compatible for measuring the audio signal, for example, rubber, a polyester reinforcing member or a thin urethane layer. The protective layer can also be combined with an adhesive for mounting the audio sensor on or near a surface of the skin. Additionally, shielded and low-noise elements can be used to minimize the amount of ambient noise and interference detected by the audio sensor.

Figure 6:
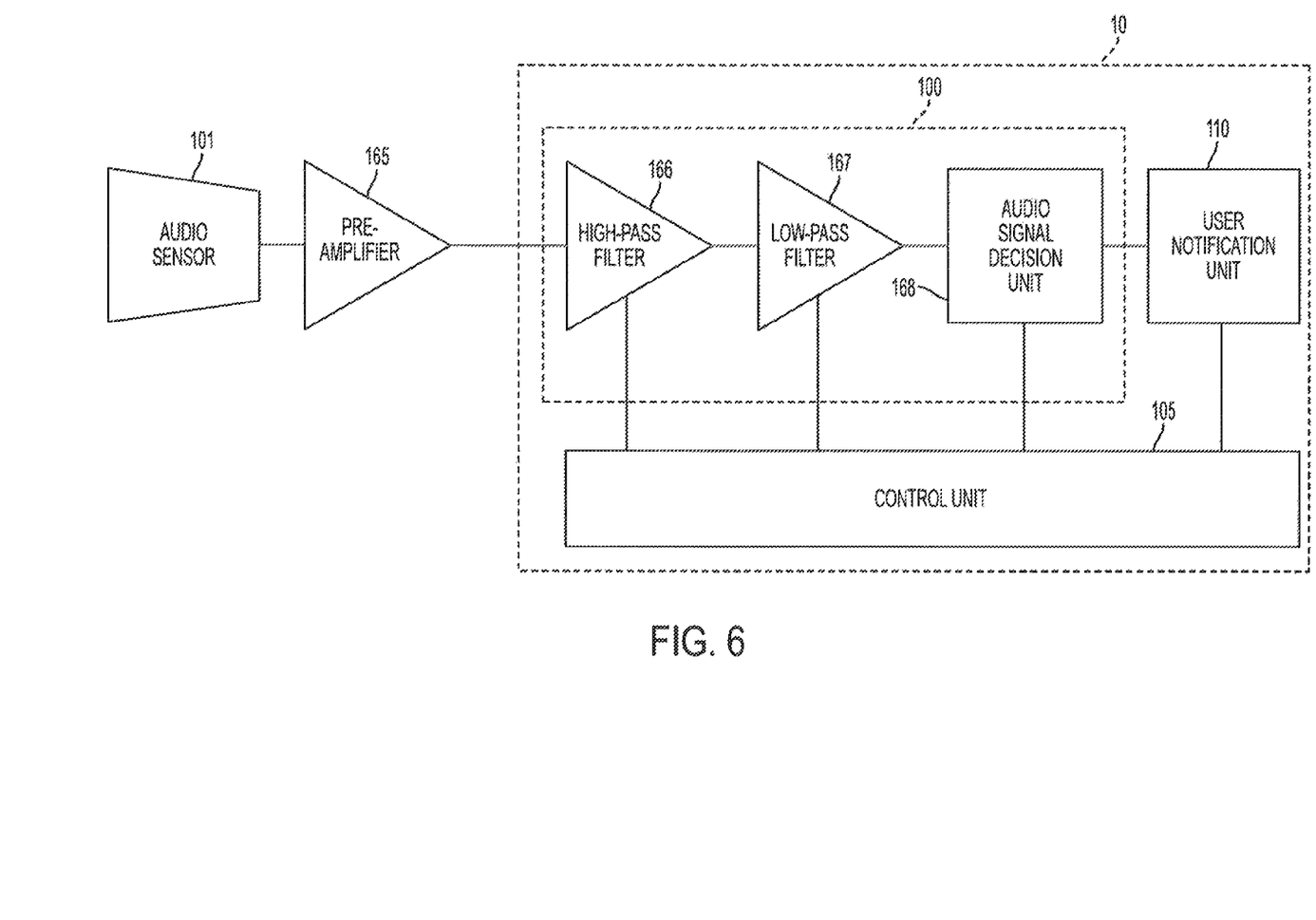
FIG. 6 is a block diagram of audio signal processing according to an example embodiment.

Referring to FIG. 6, detected audio signals are transmitted to the audio signal processing unit 100 and processed for determining whether or not the catheter tip 183 is in the target location. In one example embodiment, the audio frequency range associated with the sound wave generated by a saline bolus is identified. A high-pass filter 166 and a low-pass filter 167 are implemented to remove any frequencies outside of that range, such as audio frequencies detected from breathing, blood flow, body movement or ambient environmental noise. A preamplifier 165 can also be connected to the audio sensor to amplify the detected audio signal. Once frequencies outside of the desired frequency range are filtered out, an audio signal decision unit 168 determines if the remaining isolated frequencies representing the saline bolus are above a predetermined threshold.

The predetermined threshold can be set based on various factors corresponding with the catheter tip being located in the target location, including for example a comparison to a baseline audio signal. The baseline audio signal can be established by detecting an audio signal from the audio sensor before or after the saline bolus is injected. The detected baseline audio signal can be transmitted to the audio signal processing unit 100 and stored in memory. The baseline audio signal can also be manually programmed into the memory of the audio signal processing unit 100. The above described technique audio signal processing is one of many known in the art, however, any compatible technique can be used according to the present invention.

Figure 7:
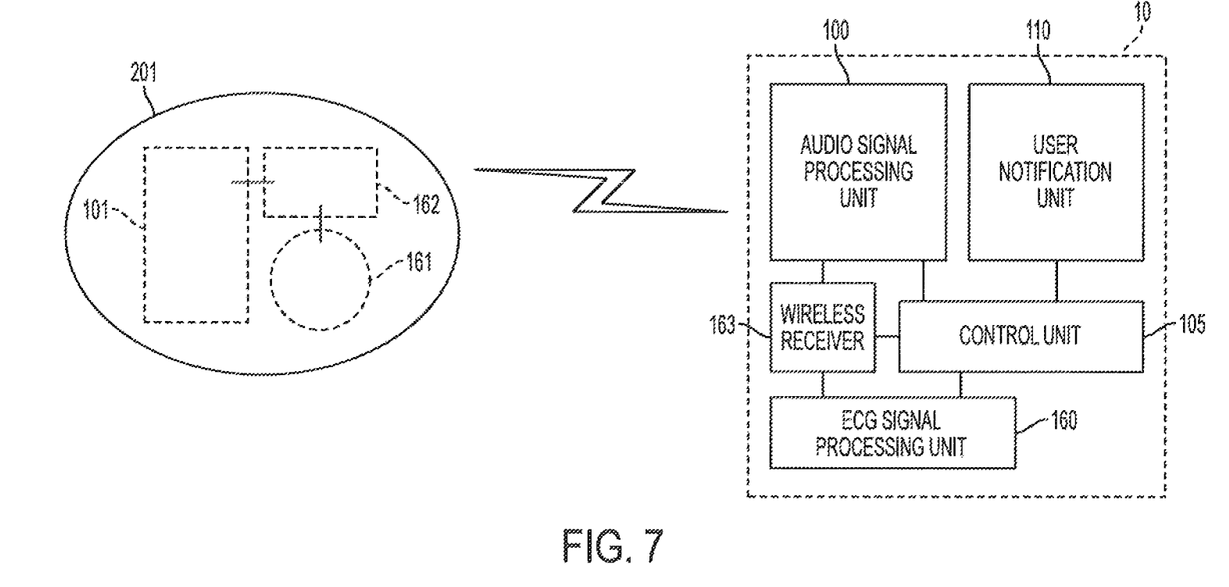
FIG. 7 illustrates an electrocardiogram electrode and an audio sensor communicating wirelessly with a user console according to an example embodiment.

Referring to FIG. 7, in an alternative embodiment, an electrocardiogram electrode 161 can be incorporated into the protective layer 201 for tracking electrical activity of the heart. As already known in the art, electrocardiograms can be used for locating catheter tip locations near the heart by tracking the change of the P wave as the catheter is advanced from the upper ⅓ of the superior vena cava down to through the lower ⅓ of the superior vena cava, and into the right atrium 171. The change in the P wave on an electrocardiogram monitor correlates to the position of the catheter tip, typically spiking as the catheter tip enters the right atrium 171. The P wave is reduced as the catheter tip is pulled back from the entrance to the right atrium 171. Thus, the reduced P wave should indicate that the catheter tip is terminated at the junction of the right atrium and the superior vena cava. In the present embodiment, an electrocardiogram electrode 161 is positioned in the protective layer 201 next to the first audio sensor 101. The electrocardiogram electrode 161 transmits detected electrocardiogram signals to the electrocardiogram signal processing unit 160. The signal is processed and a control unit 105 can verify that the catheter tip location determined by the audio signal processing unit 100 is consistent with the catheter tip location determined by the electrocardiogram signal processing unit 160. Transmission of the electrocardiogram signal and detected audio signal can be by a wireless transmitter 162. The wireless transmitter 162 can be built into the protective layer 201 and can communicate with a wireless receiver 163 built into the user console 10. The electrocardiogram electrode 161 can also detect a signal before or after the saline bolus is administered for monitoring the heartbeat or establishing an electrocardiogram baseline.

The user console 10 can be a stationary unit, or a mobile unit such as a handheld device. Further, the audio signal processing unit 100, control unit 105, user notification unit 110 and electrocardiogram signal processing unit 115 can be implemented in hardware, software, or some combination. For example, in a wireless transmission embodiment, the user console 10 is a handheld tablet device, and the audio sensors transmit the measured audio signals to the handheld tablet device using a wireless protocol such as Bluetooth. The user notification unit 110 could incorporate the display of handheld tablet device to communicate with the user.

Although a saline bolus has been used in example embodiments, the present invention is not limited to requiring a saline bolus. Any fluid infused from a catheter tip will generate an audio signal. Other fluids may include heparin based solutions, including for example Lactated Ringer's solution and Hartmann's Solution. With respect to infusion rates, although a bolus or rapid infusion of fluid will improve clarity of the detected audio signal, infusion rates may vary depending on various factors including the pickup ability of the audio sensors. Further, the audio signal processing unit 100 can be programmed to compensate for changes in fluids and infusion rates.

Figures 8A, 8B:
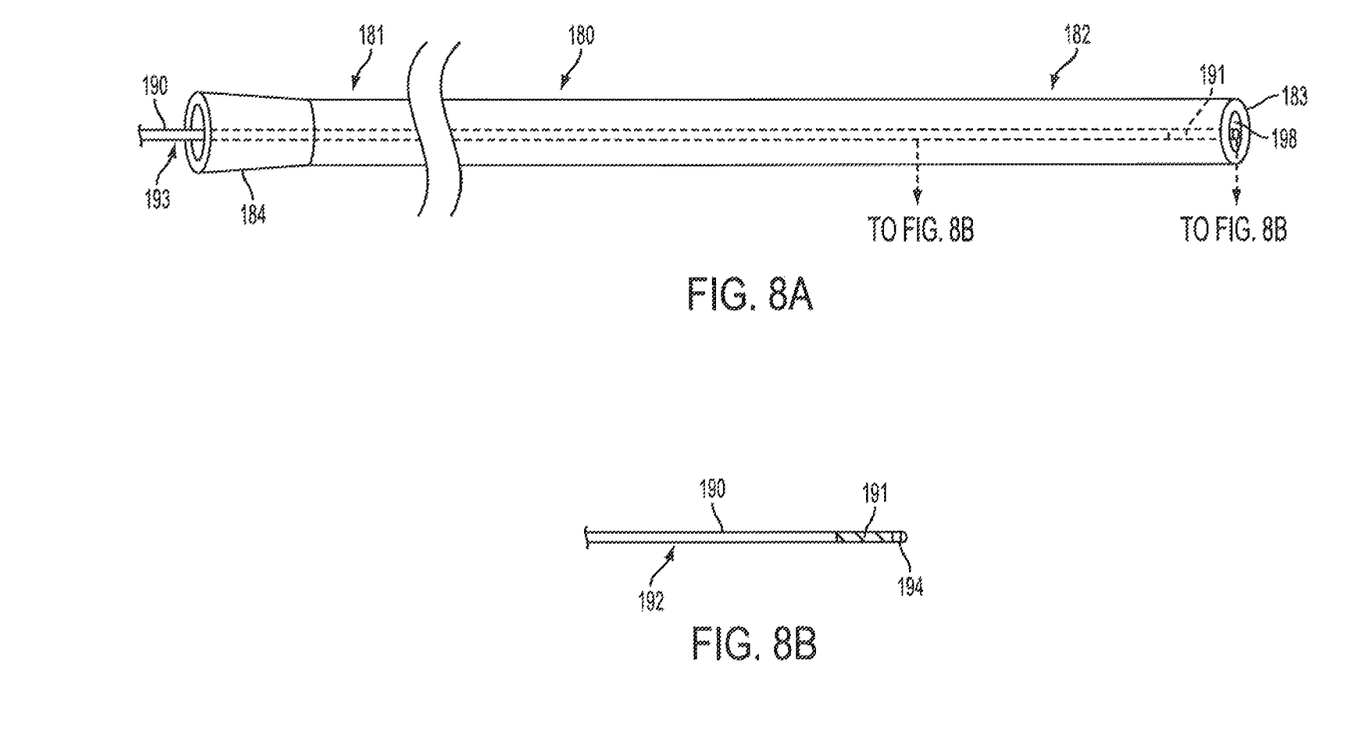
FIG. 8A is a side view of a catheter with a flexible elongated member having a piezo audio emitting element configured at the distal portion extended through a lumen in the catheter.
FIG. 8B is a side view of the distal portion of the flexible elongated member having a piezo audio emitting element.

In an alternative embodiment, a method for locating a catheter tip 183 using audio detection uses an audio emitting element positioned at the catheter tip 183, thus no fluid infusion is required. In an example embodiment shown in FIGS. 8A and 8B, a flexible elongated member 190 has a proximal portion 193 and distal portion 192, terminating in a tip 194 at the distal portion192. Proximate to the tip 194 is an audio emitting element 191, such as a piezo crystal or a piece of piezo film. The flexible elongated member 190 can be made of a medical grade flexible material having a diameter smaller than the diameter of the lumen 198 in the catheter 180. The regions along the flexible elongated member 190 can vary in stiffness, depending on the application. The flexible elongated member 190 may also be made from a guide wire like material. According to the present embodiment, the user console 10 can communicate with the audio emitting element 191 through communication elements such as conductive wire or ink that extend through the flexible elongated member 190. The communication elements can extend to the proximal portion 193 of the flexible elongated member 190, and can be connected to an audio signal generating unit in the user console 10. The audio signal generating unit can set the audio emitting element 191 to emit an audio beacon signal at a frequency distinct from the audio frequencies of ambient noise. For example, consideration should be given to blood flow, breathing, bodily movements and ambient environmental noise. Consideration should also be given to audio sensor position and the impact that anatomical factors such as body density and bone structure will have on detection of particular beacon frequencies. According to this method, the location of any catheter tip can be located, regardless of length, size or manufacturer.

Figures 8C, 8D:
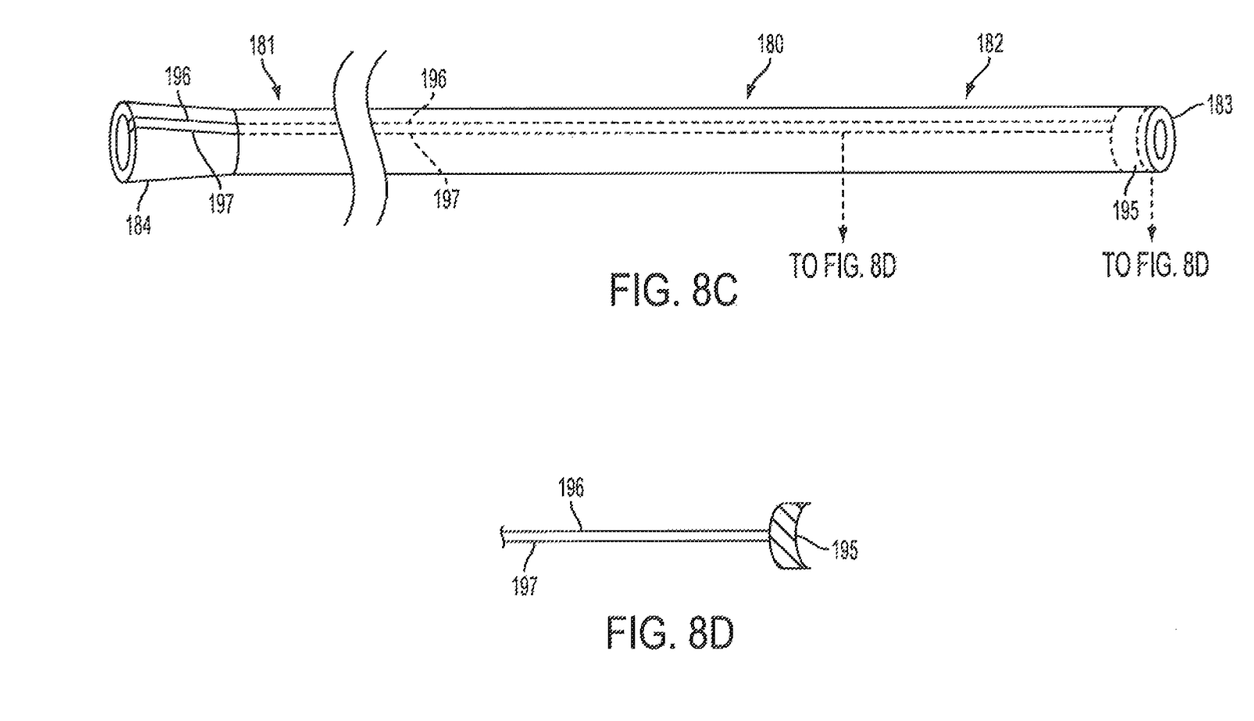
FIG. 8C is a side view of a catheter having a piezo film audio emitting element configured at the distal portion.
FIG. 8D is a side view of a piezo film element with communication elements extending proximally.

Alternatively, the sound emitting element can be attached to the catheter. In the example embodiment shown in FIGS. 8C and 8D, an audio emitting element 195 such as piezo film is attached to or embedded in a wall of the catheter distal end portion 182. A first and second elongated transmission element 196 and 197 extend from the sound emitting element proximally through the catheter wall, exiting the catheter at its proximal end. The exposed communication elements at the luer 184 can be connected to an audio signal generating unit in the user console 10. The user console 10 can thus communicate with the audio emitting element 195 to set an audio beacon signal at a distinct audio frequency. According to these methods for locating the catheter tip, a saline bolus or infusion of fluid from the catheter tip is not required, since the sound emitting element acts as a beacon for the audio sensors. Further, the location of a catheter tip can be determined on initial placement and subsequent maintenance, and does not require a separately stocked stylet component.

Some or all of the components mentioned above could be included in a kit. The kit may include a user console, audio sensors, wired or wireless signal transmission elements, and instructions for use. The kit may also include PICC catheters with or without an audio emitting element, and a stylet with an audio emitting element.

Although it is common to have the catheter tip terminate in a lower ⅓ of the superior vena cava, or at the junction of the superior vena cava and the right atrium, the method according to the present invention can be used for procedures that target any site within the body. Further, any type of catheter tip can be located, including acute and chronic dialysis catheters, subcutaneous port catheters, and central venous catheters. In addition, access sites do not need to be in the arm. For example, for a patient with amputated arms, the access site may be in the groin or in the back.

What is claimed is:

1. A method for locating a catheter tip within a human body comprising:
    inserting a catheter into a hollow anatomical structure of the human body, wherein the catheter comprises
        an elongated body having proximal end and a distal end terminating in a catheter tip at the distal end,
        a lumen having an opening disposed at the distal end, and
        an audio emitting element configured at a distal portion of the elongated body;
    advancing the catheter at least partially through the hollow anatomical structure;
    positioning a first audio sensor at a first site on or near the human body;
    emitting an audio beacon signal from the audio emitting element;
    detecting a first audio signal through the first audio sensor;
    transmitting the first audio signal to an audio signal processing unit;
    determining if the first audio signal corresponds to a target location of the catheter tip; and
    transmitting a notification signal to a user notification unit.

2. The method of claim 1, further comprising:
    detecting a baseline audio signal through the first audio sensor,
    transmitting the baseline audio signal to the audio signal processing unit, a comparing the baseline audio signal to the first audio signal.

3. A method for locating a catheter tip within a human body comprising:
    inserting a catheter into a hollow anatomical structure of the human body, wherein the catheter comprises
        an elongated body having a proximal end and a distal end terminating in a catheter tip at the distal end, and
        a lumen having an opening disposed at the distal end, and
    positioning an audio emitting element at or near the catheter tip;
    advancing the catheter at least partially through the hollow anatomical structure;
    positioning a first audio sensor at a first site on or near the human body;
    emitting an audio beacon signal from the audio emitting element;
    detecting a first audio signal through the first audio sensor;
    transmitting the first audio signal to an audio signal processing unit;
    determining if the first audio signal corresponds to a target location of the catheter tip; and
    transmitting a notification signal to a user notification unit.

* * * * *